United States Patent
Daich et al.

(12)

(10) Patent No.: US 11,324,639 B2
(45) Date of Patent: May 10, 2022

(54) NEGATIVE PRESSURE WOUND TREATMENT SYSTEM AND METHOD

(71) Applicant: The Brigham and Women's Hospital, Inc., Boston, MA (US)

(72) Inventors: Julian Daich, Cambridge, MA (US); Giorgio Giatsidis, Brookline, MA (US); Dennis P. Orgill, Belmont, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 781 days.

(21) Appl. No.: 15/761,659

(22) PCT Filed: Sep. 21, 2016

(86) PCT No.: PCT/US2016/052817
§ 371 (c)(1),
(2) Date: Mar. 20, 2018

(87) PCT Pub. No.: WO2017/053384
PCT Pub. Date: Mar. 30, 2017

(65) Prior Publication Data
US 2018/0344534 A1 Dec. 6, 2018

Related U.S. Application Data

(60) Provisional application No. 62/221,342, filed on Sep. 21, 2015.

(51) Int. Cl.
*A61F 13/06* (2006.01)
*A61M 1/00* (2006.01)
*A61F 13/00* (2006.01)

(52) U.S. Cl.
CPC ...... *A61F 13/067* (2013.01); *A61F 13/00063* (2013.01); *A61F 13/00068* (2013.01);
(Continued)

(58) Field of Classification Search
CPC .............. A61F 13/067; A61M 1/0035; A61M 1/0072; A61M 1/009; A61M 2205/078;
(Continued)

(56) References Cited

U.S. PATENT DOCUMENTS 7,618,382 B2 * 11/2009 Vogel .................... A61F 13/069
601/10
7,867,206 B2 1/2011 Lockwood
(Continued)

OTHER PUBLICATIONS

Brem, H, et al.. Cellular and molecular basis of wound healing in diabetes; J Clin Invest. May 1, 2007; 117(5): 1219-1222.
(Continued)

*Primary Examiner* — Andrew J Mensh
(74) *Attorney, Agent, or Firm* — Quarles & Brady LLP (57) ABSTRACT

A negative pressure wound treatment system comprising a bandage portion and a negative pressure portion. The bandage portion includes a dressing portion in contact with a wound and a sealing layer positioned in contact with the dressing portion. The sealing layer includes an adhesive creating a seal around the wound. The negative pressure portion is in fluid communication with the bandage portion and includes a first valve and a second valve. The first valve is in fluid communication with the bandage portion and the negative pressure portion. The second valve is in fluid communication with the negative pressure portion and the surrounding environment. The negative pressure wound treatment system is configured to provide negative pressure to an area sealed by the bandage portion upon the actuation of the negative pressure portion. The negative pressure portion is configured to be actuated by compressing the negative pressure portion while walking.

23 Claims, 7 Drawing Sheets

(52) U.S. Cl.
CPC .............. *A61M 1/743* (2021.05); *A61M 1/82* (2021.05); *A61M 1/90* (2021.05); *A61M 1/962* (2021.05); *A61M 2205/078* (2013.01); *A61M 2205/3344* (2013.01); *A61M 2205/3561* (2013.01); *A61M 2205/3584* (2013.01); *A61M 2210/086* (2013.01); *A61M 2230/63* (2013.01)

(58) Field of Classification Search
CPC .... A61M 2205/3344; A61M 2210/086; A61M 2230/63
USPC .......................................................... 604/319
See application file for complete search history.

(56) References Cited

U.S. PATENT DOCUMENTS

| | | | | |
|---|---|---|---|---|
| 7,896,823 | B2* | 3/2011 | Mangrum | A61H 9/005 601/9 |
| 8,444,611 | B2 | 5/2013 | Sanders | |
| 8,603,013 | B2 | 12/2013 | Randolph | |
| 9,039,678 | B2 | 5/2015 | Saxena | |
| 9,827,403 | B2 | 11/2017 | Coward | |
| 2004/0163278 | A1* | 8/2004 | Caspers | A43B 17/035 36/3 R |
| 2007/0055209 | A1* | 3/2007 | Patel | A61M 1/0088 604/315 |
| 2009/0234249 | A1* | 9/2009 | Randolph | A43B 7/00 600/592 |
| 2013/0116661 | A1* | 5/2013 | Coward | A61M 1/0066 604/543 |
| 2014/0171837 | A1* | 6/2014 | Harcourt | A61F 5/05833 601/7 |
| 2014/0228792 | A1* | 8/2014 | Weston | A61M 1/90 604/321 |
| 2014/0343517 | A1* | 11/2014 | Jameson | A61F 13/00068 604/319 |

OTHER PUBLICATIONS

Gudmundsdottir I, et al., Negative pressure wound therapy—review; Laeknabladid. Apr. 2014;100(4):219-24.(English summary on final page).

Ljubola, D.The Bulb Vacuum System (BVS)—Negative Pressure Therapy for Healing Acute and Chronic Wounds in Underdeveloped Areas. 2012 Accesed online at: http://web.stanford.edu/group/journal/cgi-bin/wordpress/wp-content/uploads/2012/09/Ljuboja_Eng_2012.pdf.

Zhong S.P., et al., Tissue scaffolds for skin wound healing and dermal reconstruction; 1Wiley Interdiscip Rev Nanomed Nanobiotechnol. Sep.-Oct. 2010;2(5):510-25.

Boulton AJ, et al., The global burden of diabetic foot disease; Lancet. Nov. 12, 2005;366(9498):1719-24.

Stockl K., et al., Costs of lower-extremity ulcers among patients with diabetes; Diabetes Care. Sep. 2004;27(9):2129-34.

Moulik, P.K., et al., "Amputation and mortality in new-onset diabetic foot ulcers stratified by etiology." Diabetes care 26.2 (2003): 491-494.

Huang C, et al., Effect of negative pressure wound therapy on wound healing; Curr Probl Surg. Jul. 2014;51(7):301-31.

Scherer SS, et al., The mechanism of action of the vacuum-assisted closure device; Plast Reconstr Surg. Sep. 2008;122(3):786-97.

International Search Report and Written Opinion for PCTUS1652817, 15 pages, dated Dec. 15, 2016.

* cited by examiner

NEGATIVE PRESSURE WOUND TREATMENT SYSTEM AND METHOD

CROSS REFERENCE TO RELATED APPLICATIONS

This application represents the national stage entry of PCT International Application PCT/US2016/052817 filed Sep. 21, 2016, which claims benefit of U.S. Provisional Application 62/221,342 filed Sep. 21, 2015, all of which is incorporated herein in its entirety by reference.

STATEMENT REGARDING FEDERALLY SPONSORED RESEARCH

Not applicable

SEQUENCE LISTING

Not applicable

BACKGROUND OF THE INVENTION

Field of the Invention

The present disclosure generally relates to a wound treatment system and method, and more specifically, to a negative pressure wound treatment system and method for treating wounds with negative pressure generated by a user walking while wearing a device.

Description of the Background of the Invention

Negative pressure wound therapy (NPWT) is a treatment that aids in the healing of wound injuries by increasing blood flow to the target area and promoting the formation of granulation tissue. It also functions in removing and draining fluid and leakage, diminishing both the amount and rate of infection and bacterial growth, assisting in closure, and providing protection from the surrounding environment. Such a device typically is comprised of: 1) a gauze or wound dressing to fill the cavity, 2) a drainage tube held near the area of injury, sometimes inside of the dressing, 3) an adhesive sealant placed atop the dressing to create an air tight seal, 4) a container or outlet for the fluid drained from the injured area, and 5) a low-pressure vacuum to create negative pressure. The dressing of the wound requires frequent replacement. According to the Food and Drug Administration, NPWT is proven to provide aid to chronic wounds, burns, diabetic and pressure ulcers, acute wounds, traumatic wounds and dehisced wounds. In addition negative pressure can locally induce or mimic the therapeutic effects of massage.

A special case of wounds are diabetic foot ulcers (DFUs). DFUs are a leading cause of lower limb amputations. Diabetes affects hundreds of millions of people worldwide, including tens of millions of patients in US, and are projected to double by 2030. DFUs are a primary cause of hospital admissions in the developed world and one of the most impaired conditions associated with diabetes, often leading to pain, suffering, and a poor quality of life for patients. DFUs precede a significant majority of all diabetes-related lower-leg amputations and are characterized by impaired healing.

Portable NPWT devices have been proposed in the art, however many require an external power supply for creating negative or positive air pressure. Another disadvantage of the devices described in the art is that patients cannot wear them for natural walking. Some of the prior art devices that can be worn while walking require the entire foot and lower leg to be sealed and covered, resulting in comfort issues. Further still, other devices in the prior art require a hand powered device that is to be used at developing areas, but the operation requires active patient activity and attention.

Therefore, there is a need for a NPWT system that overcomes one or more of the aforementioned drawbacks of NPWT devices known in the art. In particular, there is a need for a NPWT system and method that generates low pressure by introducing means under a foot of the user configured to be actuated by walking and the area treated is specific to an area slightly larger than one or more DFU's positioned on a lower extremity of the user.

SUMMARY OF THE INVENTION

A negative pressure wound treatment system includes a bandage portion and a negative pressure portion. The bandage portion includes a dressing portion in contact with a wound and a sealing layer positioned in contact with the dressing portion. The sealing layer creates a seal around the wound. The negative pressure portion is in fluid communication with the bandage portion and includes a first valve and a second valve. The first valve is in fluid communication with the bandage portion and the negative pressure portion. The second valve is in fluid communication with the negative pressure portion and the surrounding environment. The negative pressure wound treatment system is configured to provide negative pressure to an area sealed by the bandage portion upon the actuation of the negative pressure portion. The negative pressure portion is configured to be actuated by compressing the negative pressure portion while walking. The sealing layer may include an adhesive creating the seal around the wound.

According to another aspect of the negative pressure wound treatment system, the bandage portion and the negative pressure portion are configured as an innersole device that is positioned within a shoe of the user.

According to another aspect of the negative pressure wound treatment system, the bandage portion is sized to seal an area that is substantially the entire bottom of a user's foot.

According to another aspect of the negative pressure wound treatment system, the negative pressure portion comprises a collapsible hollow bulb.

According to another aspect of the negative pressure wound treatment system, the dressing portion comprises at least one of gauze, porous foam, and a therapeutic scaffold.

According to another aspect of the negative pressure wound treatment system, the bandage portion is sized to seal a portion of the bottom of a user's foot surrounding the wound and the negative pressure portion is positioned under an adjacent portion of the user's foot.

According to another aspect of the negative pressure wound treatment system, the bandage portion is positionable to seal an area located on a lower extremity of a user and the negative pressure portion is positionable below the user's foot.

According to another aspect of the negative pressure wound treatment system, the system includes at least one sensor.

According to another aspect of the negative pressure wound treatment system, the sensor is at least one of a pedometer and a pressure sensor.

According to another aspect of the negative pressure wound treatment system, the information collected by the sensor is at least one of recorded and broadcasted to an external device.

According to another aspect of the negative pressure wound treatment system, the valve includes a release mechanism, trigger or switch.

A wound healing device includes a first chamber and a second chamber. The first chamber includes a dressing and is configured to form a seal around a wound of a user. The dressing is in contact with the wound. The seal is around the perimeter of the first chamber. The second chamber includes at least one valve. The second chamber is in fluid communication with the first chamber through the at least one valve. Actuation of the second chamber creates a negative pressure environment in the first chamber. The second chamber is configured and positioned to be actuated by a user while walking. The seal may be formed by an adhesive around the perimeter of the first chamber.

According to another aspect of the wound healing device, the first chamber collects liquid from the wound.

According to another aspect of the wound healing device, the second chamber includes a reservoir configured to collect liquid from the wound.

According to another aspect of the wound healing device, the reservoir comprises an absorbent material.

According to another aspect of the wound healing device, the first chamber includes a reservoir configured to collect fluid from the wound.

According to another aspect of the wound healing device, the first chamber includes a reservoir configured to collect fluid from the wound and the reservoir comprises an absorbent material.

According to another aspect of the wound healing device, the second chamber is in fluid communication with the first chamber through the at least one valve, and the second chamber is in fluid communication with the surrounding environment through a second valve.

According to another aspect of the wound healing device, the at least one valve and the second valve are one-way valves.

According to another aspect of the wound healing device, the first chamber and the second chamber are configured as part of a shoe insole and the second chamber is configured to form a seal around a portion of a bottom of the user's foot and the portion includes the wound.

According to another aspect of the wound healing device, the first chamber is configured to form a seal around a wound on a portion of a user's lower extremity away from a bottom of the user's foot and the second chamber is configured to be position under a user's foot within a shoe.

According to another aspect of the wound healing device, the first chamber and the second chamber are connected via a flexible tube.

According to another aspect of the wound healing device, the second chamber is part of a shoe insole.

According to another aspect of the wound healing device, wherein any of the valves include a release mechanism, trigger or switch.

A method of treating a wound on a lower body extremity with negative pressure wound therapy includes the following steps. A first chamber is positioned over a wound on the lower body extremity and the first chamber includes a dressing configured to contact the wound. A seal is formed around the perimeter of the first chamber. A second chamber is positioned below the lower body extremity and the second chamber is configured to be actuated by the lower body extremity during walking. The first chamber is fluidly coupled to the second chamber through a first valve. The second chamber is fluidly coupled to the surrounding environment through a second valve. Actuation of the second chamber causes a negative pressure environment to be formed within the first chamber over the wound. The seal may be formed around the perimeter of the first chamber with an adhesive. However, a seal can be made without adhesives, for example, using a rubber or plastic piece as sealing and holding and pressing the perimeter with a bandage.

According to another aspect of the therapy, the method includes the second chamber positioned within a shoe and the first and second chambers are configured as an insole device sized to fit with the shoe.

According to another aspect of the therapy, the method includes the second chamber positioned within the shoe of the user and the first chamber positioned away from the shoe of the user. The first chamber is connected to the second chamber through a flexible tube.

According to another aspect of the therapy, the method includes collecting fluid from the wound in the first chamber, wherein the first chamber includes an absorbent reservoir.

According to another aspect of the therapy, the method includes collecting fluid from the wound in the second chamber, wherein the second chamber includes an absorbent reservoir.

According to another aspect of the therapy, the method includes positioning the first chamber adjacent the second chamber and the first chamber is configured to seal around the wound located on the bottom of a foot of a user. The first chamber and the second chamber are configured as components of a self-adhesive bandage.

According to another aspect of the therapy, the method includes the negative pressure environment formed within the first chamber is in the range from about 40 millimeters of mercury to about 200 mm of mercury.

According to another aspect of the therapy, the method includes that any of the valves include a release mechanism, trigger or switch.

According to another aspect of the wound healing device, a wound healing device comprises a first chamber, a second chamber and at least one valve wherein the first chamber is in contact with a wound and the second chamber exchanges fluids in care of the pressure applied by the lower extremity of a subject and the valve regulates the pressure between any of the first chamber, the second chamber, and external surroundings of the wound healing device.

According to another aspect of the wound healing device, the first chamber collects fluids from the wound.

According to a further aspect, the wound healing device includes a reservoir that collects and stores fluids from the wound.

According to another aspect of the wound healing device, the reservoir is positioned within the second chamber.

According to another aspect of the wound healing device, the reservoir includes an absorbent material.

According to another aspect of the wound healing device, the reservoir is positioned within one of the first chamber, or a duct or passage between the first chamber and the second chamber.

According to another aspect of the wound healing device, the device lacks the reservoir that collects or store fluids from the wound According to another aspect of the wound healing device, the first chamber and the second chamber are combined into one chamber for providing NPWT.

According to another aspect of the wound healing device, the first chamber and the second chamber are in fluid communication through at least one of a valve, a duct, and a flexible tube.

According to another aspect of the wound healing device, the second chamber further includes a valve in fluid communication with the surrounding environment.

According to another aspect of the wound healing device, the whole device is sized to fit within footwear of the user.

According to another aspect of the wound healing device, the first chamber is affixed to a lower extremity of a user with a mesh outside of the user's footwear.

According to another aspect any of the above devices can be applied over non wounded skin to induce therapeutic effects different from the wound healing These and other features, aspects, and advantages of the present invention will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION

Patients affected by chronic wounds are often bed-ridden due to the presence of bulky dressings and equipment which impair their ability to move and walk. This condition worsens the quality of life of the patients as well as their ability to heal since walking has a beneficial effect on lower limb microcirculation. A portable and wearable NPWT device may provide enhanced quality of life and healing benefits to patients suffering from DFU and other wounds located on the lower extremities and other parts of the body. In the embodiments disclosed hereinafter, patients may produce the low pressure or vacuum needed for NPWT just by walking with at least a portion of the wearable NPWT device under a foot. This would give patients the improved ability to maintain a healthy and improved quality of life over traditional systems. Further, no external power supply is needed and the patient's ability or capacity to move and walk during treatment would not be limited as compared to traditional methods. It has been show that negative pressure can induce therapeutic effects when applied to healthy skin. It can create a suction effect that increases blood and lymphatic circulation systemically and to the local area, relaxes muscle tissue and support, draws stagnation, pathogenic factors and toxins out of the body and releases a myriad of pain causing factors. A common application of these effects are known from several years in techniques as cupping that can even being combined with massage along with the movements performed and areas treated by a therapist will produce stimulating (toning) or sedating (draining) effects. Conditions as chronic venous insufficiency (CVI) or plantar fasciitis, the present invention can be employed in addition to other physiotherapy surgery, drug treatment and sclerotherapy, with both prophylactic and curative intent. Apart from improving the hemodynamic situation, localized negative pressure therapy aims in particular to preserve or reactivate the active and passive pump mechanisms of the lower limbs, for example, the calf muscle pump and the ankle pump. In addition, localized negative pressure can help desensitize those areas affected by neurogenic pain as foot neuropathy as a complement or in replacement of traditional massage. In lymphedema, tissue fluid steadily accumulates in the subcutaneous space containing loose connective tissue. Since there is no force that could mobilize and propel stagnant fluid to the regions where lymphatics absorb and contract, this task should be taken over by external massage or forces. In one embodiment, negative pressure can be applied one the skin surface of the affected region redirecting fluids and restoring lymphatic function. In a similar manner some of the devices described can be used to treat edema.

In one embodiment at least one of the valves can be activated or deactivated by a release mechanism, trigger or switch, thus creating different cycles of presence or absence of negative pressure over the interest area. The release mechanism, trigger or switch can be electric or mechanic and even can be activated remotely or triggered by an external device or timer. In a more specific embodiment, the release mechanism, trigger or switch includes a pressure sensor that enables the application of negative pressure can be regulated or determined by a threshold.

Figure 1:
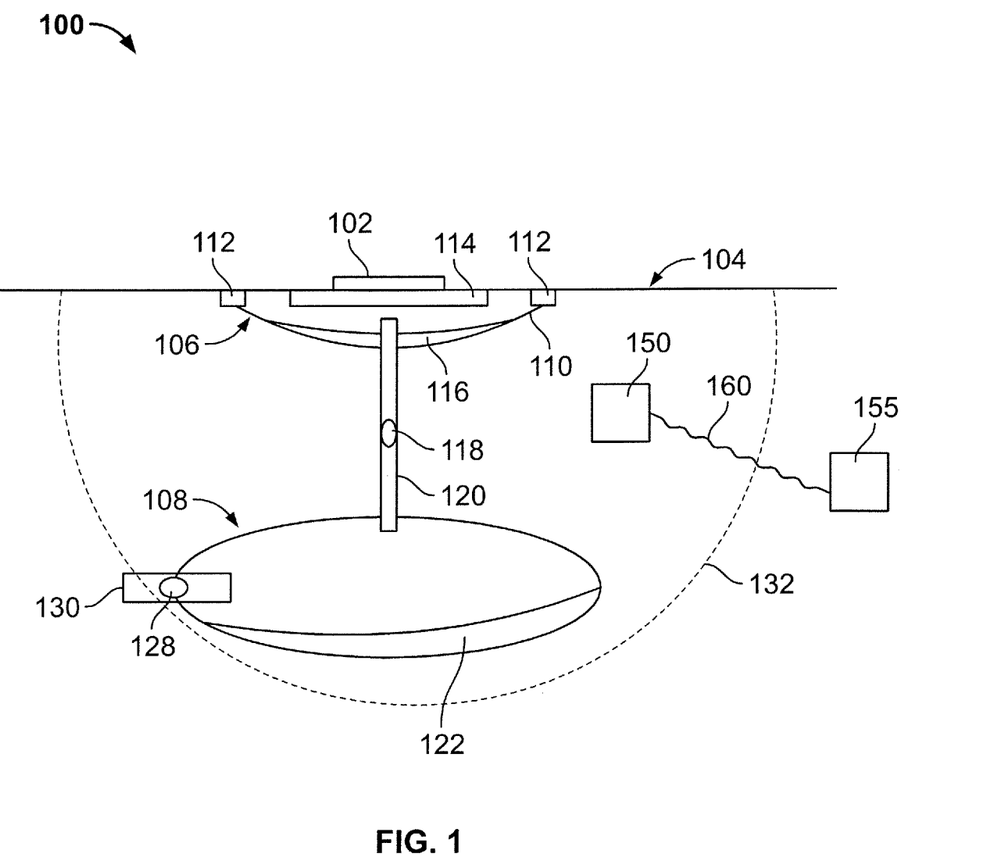
FIG. 1 is a schematic representation of a NPWT system.

Referring to FIG. 1, a schematic embodiment of a negative pressure wound treatment system 100 according to the invention for providing negative pressure wound therapy is depicted. The treatment system 100 is shown covering a wound 102 located on a body portion 104 of a patient. The wound 102 may be a chronic wound, a DFU, a burn or any type of wound that one having ordinary skill in the art would understand as appropriate for NPWT. The body portion 104 may be located on the sole of a patient's foot or any other portion of a patient's body including but not limited to the lower extremities. As will be disclosed later, different embodiments will demonstrate treatment of wounds positioned away from a patient's foot while walking generates the necessary conditions for successful NPWT.

Still referring to FIG. 1, the treatment system 100 includes a first chamber or bandage portion 106 and a second chamber or negative pressure portion 108. The first chamber 106 includes a sealing layer 110 that forms an air-tight seal over the wound 102 and a small area around the wound. The sealing layer 110 may form the seal over the wound 102 by application of an adhesive 112 around the perimeter of the sealing layer 110. It is contemplated that the sealing layer 110 may be a flexible layer of any shape that facilitates the coverage of the wound 102. For example, the shape and type of materials used for the sealing layer 110 may be optimized depending on the location placed on the body of the patient. In some embodiments, the sealing layer 110 may be formed from a rigid or semi-rigid material that is secured by adhesive 112 around the perimeter of the sealing layer 110. Alternatively, a sealing layer 110 may be attached and form a seal on the body portion 104 by other methods involving adhesive 112. For example, a tape layer (not shown) may be placed over the sealing layer 110 that extends around the sealing layer 110 to form an air-tight seal over the wound 102. Further, the sealing layer may be formed by spreading an adhesive that forms the sealing layer 110 and thus creates the first chamber 106. One non limiting example of adhesive can be cyanoacrylate or its derivatives. One having ordinary skill in the art would understand the various ways adhesive 112 could be applied to flexible and rigid or semi-rigid materials to form an air-tight seal over a wound 102.

Continuing to refer to FIG. 1, the first chamber 106 may include a dressing portion 114. The dressing portion is positioned to be in contact with the wound 102 and the sealing layer 110. It is contemplated that the dressing portion may comprise any number of materials or combination of materials. Some not limiting examples would be traditional gauze and bandage materials, porous foam, and therapeutic or regenerative scaffolds. The dressing portion 114 may be any combination of these or other materials. In some embodiments, the first chamber may include a reservoir 116 for the collection of fluids from the wound 102. The reservoir 116 may include an absorbent material in contact with the dressing portion 114. Non limiting examples of absorbent materials can include gauze and bandage, nafion or a combination thereof. Alternative embodiments can avoid this chamber for fluid collection, for example when applied to wounds that have no significant liquid excretions.

The second chamber 108 is in fluid communication with the first chamber 106 through a first valve 118. The first valve 118 may be positioned within the first chamber 106, within the second chamber 108, or in a tube 120 that connects the first chamber 106 to the second chamber 108. In some embodiments, the tube 120 may be just a duct and the first chamber 106 and the second chamber 108 may be in very close proximity and or contact with each other. In other embodiments, the tube 120 may be longer allowing the first chamber 106 to be spaced a distance away from the second chamber 108. It is contemplated that the distance between the first chamber 106 and the second chamber 108 can vary based on the application and the location of the wound 102 to be treated. As will be shown in later embodiments, the first chamber 106 may be placed adjacent to the second chamber 108 or the first chamber 106 may be placed away from the second chamber 108.

Still referring to FIG. 1, the second chamber 108 may also include a reservoir 122 for the collection of fluids from the wound 102. The reservoir 122 may be positioned within the second chamber 108 in any orientation or location favorable for the collection of fluid. The reservoir 122 may be formed from absorbent material placed within the second chamber 108. Alternatively, it is contemplated that in some embodiments a separate reservoir may be formed from a third chamber (not shown) that is positioned between the first chamber 106 and the second chamber 108 for the purpose of collecting fluids from the wound 102. It is also contemplated that the first chamber 106, the second chamber 108, and the third chamber (not shown) are in fluid communication with each other. Further, in some embodiments the third chamber (not shown) may include absorbent materials (not shown) disposed within the third chamber (not shown). The tube 120 may be divided into two sections (not shown)) connecting the third chamber (not shown) to the first chamber 106 and the second chamber 108.

The second chamber 108 also includes a second valve 128 that may be placed in a duct 130 that provides fluid communication between the second chamber 108 and the surrounding environment. It is also contemplated that the second chamber 108 is constructed of a resilient but compressible material. As will be detailed later, the actuation (i.e., the application and removal of a compressive force) of the second chamber creates the low pressure environment in the first chamber 106 for the NPWT. It is contemplated that the actuation of the second chamber 108 will result in a low pressure environment in the first chamber 106 that is in the range from about 40 millimeters of mercury (mm of Hg) to about 200 mm of Hg, or in the range from about 80 millimeters of mercury (mm of Hg) to about 140 mm of Hg. It is contemplated that the low pressure created within the first chamber 106 may be tuned or adjusted by the use of different second chambers 108, first valves 118, or second valves 128. The treatment system 100 may include an outer cover 132. It is contemplated that the outer cover 132 may take different forms in the different embodiments disclosed below. The outer cover 132 may assist in retaining the treatment system 100 or portions of the treatment system 100 in place on the patient. The outer cover 132 may include adhesive for securing portions of the treatment system 100 in place or may comprise a wrap that would wrap around a foot or lower extremity portion of a patient.

Still referencing FIG. 1, the general operation of the treatment system 100 is disclosed. The first chamber 106 is positioned over a wound 102 and the dressing portion 114 is positioned in contact with the wound 102. A seal is foamed around the perimeter of the first chamber with adhesive 112. The second chamber 108 is positioned below a foot of the patient. The first chamber 106 is fluidly coupled to the second chamber 108 through the first valve 118. The second chamber 108 is fluidly coupled to the surrounding environment through the second valve 128. The patient begins walking. As the patient steps onto the foot with the second chamber 108 positioned below it, a compressive force is applied to the second chamber 108. As the second chamber 108 is compressed, air within is pushed out through the second valve 128. Upon the release of the compressive force, the resilient nature of the second chamber 108 causes the second chamber 108 to revert to the original uncompressed shape and a low pressure environment is created. The low pressure in the second chamber 108 will then draw air and possibly fluid from the first chamber 106 through the first valve 118 creating a lower pressure environment in the first chamber 106. It is contemplated that the compression of the second chamber 108 is only partial and that several cycles of compression may be required for the first chamber to reach the desired low pressure range for NPWT as described above. Eventually, the pressure in the first chamber 106 will be low enough to provide the therapeutic benefits of NPWT to the wound 102. The pressure in the first chamber may eventually reach equilibrium with the resilient nature of the second chamber 108 such that the second chamber remains partially compressed even after the compressive force is removed. As the pressure increases in the first chamber 106 however, the second chamber 108 may partially uncompress and draw air and fluid from the first chamber 106 thus maintaining a low pressure environment in the first chamber 106. The positioning of the second chamber 108 under the sole can vary according to the embodiment and use.

It is also contemplated that the first valve 118 and the second valve 128 may include a release mechanism that is accessible by the user. In this way the user can create different cycles of the presence or absence of negative pressure over the area of interest. It is further contemplated that the release mechanism may be a trigger or a switch.

It is contemplated that the duration of time that the treatment system 100 may be used to treat a wound 102 depends on numerous variables. In some embodiments, all of the components may be sized such that any absorbent materials within the first chamber 106 and the second chamber 108 may become saturated from fluids from the wound 102 in a few hours. In some embodiments the time period may be between about 3 hours to about 6 hours, or about 3 hours to about 12 hours, or about 3 hours to about 24 hours. Alternatively, the time period may be extended to multiple days depending on the size of the components and the nature and condition of the wound.

Still referring to FIG. 1, it is contemplated that the treatment system 100 may include at least one sensor 150 in communication with at least one external device 155. The communication (represented by a line 160) between the at least one sensor 150 and the external device 155 may be by a wired or wireless process. One having ordinary skill in the art would recognize the multitude of ways the at least one sensor 150 could send or transmit information to the at least one external device 155. It is contemplated that the at least one sensor could be a wide variety of sensor types that may provide a wide variety of useful data to the patient and/or a healthcare provider monitoring the patient. In one exemplary embodiment, the sensor 150 may be a pressure sensor the determines the pressure level achieved in the first chamber 106 while the patient is walking and/or not walking. In another exemplary embodiment, the sensor 150 may include the ability to determine the number of times the second chamber 108 has been actuated to generate negative pressure in the first chamber 106. Further embodiments may include external devices 155 that is at least one of a pedometer, a smart phone, a smart wearable device (e.g., a watch) that is capable of receiving communications from the at least one sensor 150. It is further contemplated that the external device may be capable of at least recoding and or displaying the data. Some embodiments may include the external device 155 communicating the data received from the sensor 150 to other external devices via a variety of means (e.g., a cellular data connection, a Wi-Fi connection, a wired internet connection, a Bluetooth connection). It is also contemplated that the health care provider may monitor the data transmissions from the patient in person or remotely via electronic transmissions. One having skill in the art would understand the multitude of ways via different communication protocols that the sensor 150 may communicate information to the external device 155 and in turn that information is recorded for or transmitted to the health care provider for aid in determining the effectiveness of the treatment.

Figure 2:
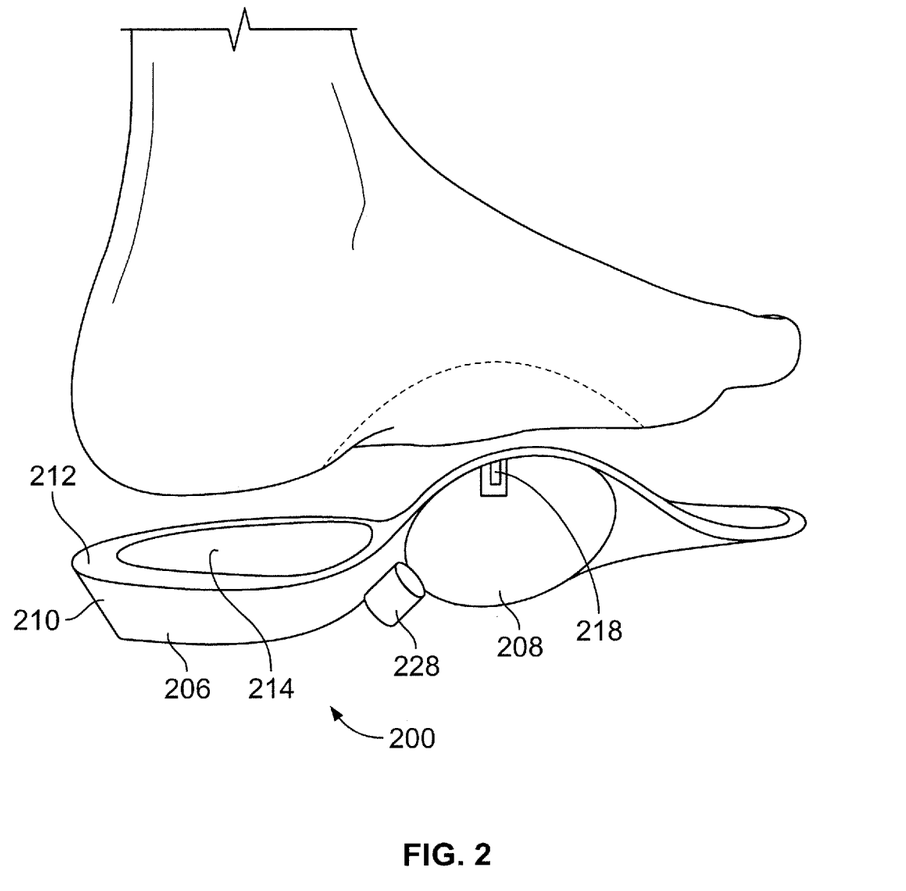
FIG. 2 is a depiction of a first embodiment of a NPWT system according to the invention.

Turning to FIG. 2, a schematic embodiment of a negative pressure wound treatment system 200 is depicted in the form of an innersole device configured to fit inside footwear of patient. The treatment system 200 includes a first chamber 206 and a second chamber 208. The first chamber 206 includes a sealing layer 210 that is in the form of an innersole of footwear that a patient may wear. The perimeter of the first chamber 206 forms a seal with an adhesive strip 212. In the present embodiment, the first chamber includes a dressing portion 214 that may contact any wounds (not shown) on the lower surface of the patient's foot. The second chamber 208 is in fluid communication with the first chamber 206 through a first valve 218. The second chamber 208 is also in fluid communication with the surrounding environment through a second valve 228. It is contemplated that the embodiment depicted in FIG. 2 may include all or some of the characteristics and features of the treatment system 100 depicted in FIG. 1.

Still referring to FIG. 2, the treatment system 200 may be configured to cover and create a low pressure environment that is substantially the entire bottom of the foot of a patient. In some embodiments, the treatment system 200 may be sized to only provide NPWT to a portion of the patient's foot. Specifically, the area sealed may only be a heel portion of the foot or some portion of the bottom of the foot larger than just the heal portion but smaller that the entire bottom of the foot.

The operation of the treatment system 200 is similar to that of treatment system 100 as described above. After a seal is created, the patient would insert the foot into footwear that is configured to receive the treatment system 200. Upon the commencement of walking, the second chamber 208 would be repeatedly compressed by the foot pressing down and create a low pressure environment within the first chamber 206. One of the advantages of the treatment system 200 would be the ability to treat multiple DFUs on the bottom of a patient's foot while providing a high level of comfort along with ease of use to the patient. Treatment system 200 may be configured to work with any footwear that includes removable innersoles, thus allowing a patient to treat wounds on the bottom of the foot while still using footwear of their own choosing.

Figure 3:
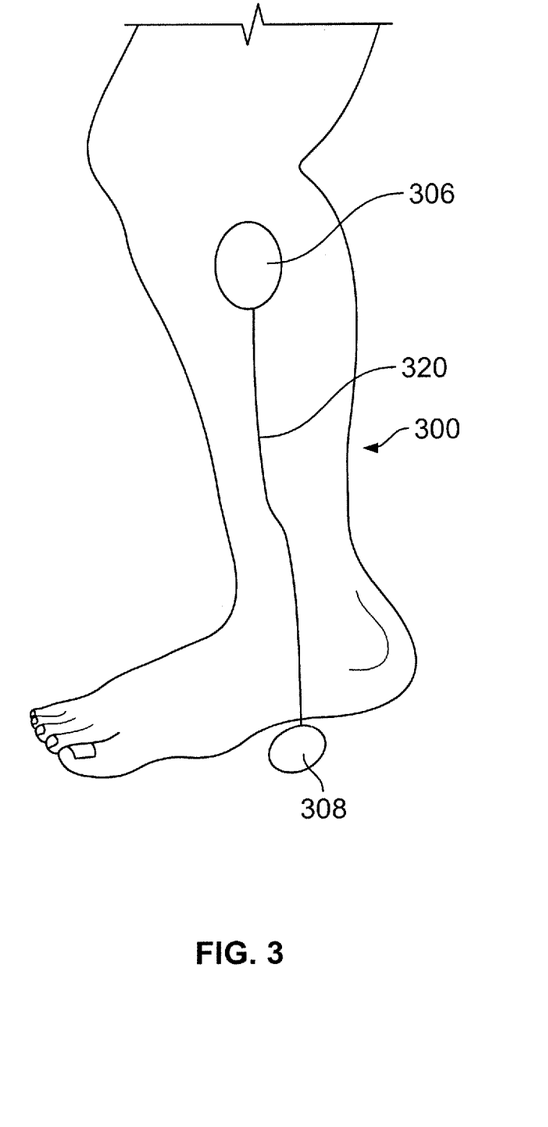
FIG. 3 is a depiction of a second embodiment of a NPWT system according to the invention.

Now referring to FIG. 3, another schematic embodiment of a negative pressure wound treatment system 300 is depicted as configured to treat a wound away from the foot of a patient. The treatment system 300 may include all or some of the characteristics and features of the treatment systems 100, 200 depicted in FIGS. 1 and 2. Treatment system 300 includes a bandage portion 306 and a negative pressure portion 308. The negative pressure portion 308 is in fluid communication with the bandage portion 306 through a first valve (not shown) and a flexible tube 320. The negative pressure portion 308 is also in fluid communication with the surrounding environment through a second valve (not shown). It is contemplated that the operation of treatment system 300 is similar to the operations already described. The patient would place the bandage portion 306 over a wound located somewhere on the body, in FIG. 3 it is depicted on a leg just below the knee. Then the negative pressure portion 308 would be placed under the foot. As the patient walks, the negative pressure portion 308 would be cyclically compressed, thus forming a low pressure environment under the bandage portion 306 and over the wound. It is contemplated that the flexible tube enables the bandage portion 306 to be placed anywhere on the body that a wound is located.

It is also contemplated that the negative pressure portion 308 may be configured in multiple ways. In some embodiments, the negative pressure portion may be configured to sit under a patient's foot within footwear of the patient's choosing. In other embodiments, the negative pressure portion 308 may be included in an innersole device or built into a footwear item. Further still, in other embodiments, the negative pressure portion 308 may be configured to be in fluid communication with multiple bandage portions 306, wherein each bandage portion 306 is located over a different wound on a different location of the body. It is contemplated that the negative pressure portion 308 may be adhesively attached to the bottom of the patient's foot or a wrap may hold it in place such that the patient is not required to wear footwear during use.

Figure 4:
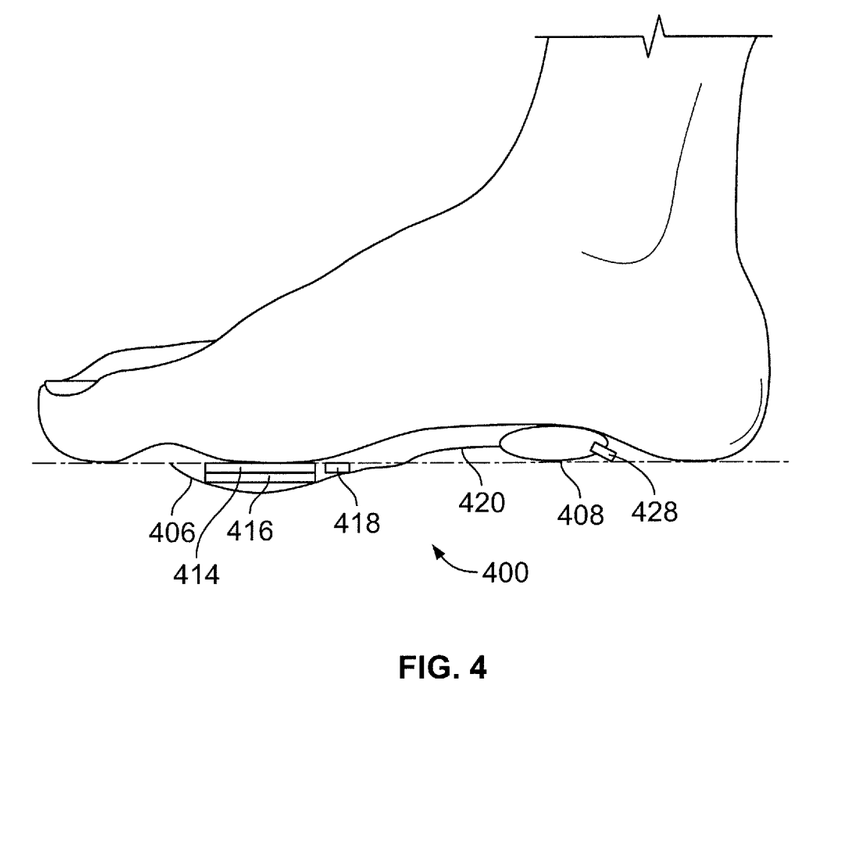
FIG. 4 is a depiction of a fourth embodiment of a NPWT system according to the invention.

Turning now to FIG. 4, another schematic embodiment of a negative pressure wound treatment system 400 is depicted in a configuration to fit under the bottom of the foot of a patient. The treatment system 400 includes a first chamber 406 and a second chamber 408. The first chamber 406 includes a dressing portion 414 and a reservoir 416. The first chamber 406 is in fluid communication with the second chamber 408 through a first valve 418 and a tube 420. The second chamber 408 is in fluid communication with the surrounding environment through a second valve 428. The treatment system 400 may include all or some of the characteristics and features of the treatment systems 100, 200, 300 depicted in FIGS. 1-3. The operation of the treatment system 400 is similar to the systems 100, 200, 300 described above. The first chamber 406 may be secured by adhesive to cover a wound on a portion of the patient's foot. The second chamber 408 may be placed under another portion of the patient's foot. Upon walking, the patient will cyclically actuate the second chamber 408 as described in the embodiments above to create a low pressure environment in the first chamber 406.

With continued reference to FIG. 4, the treatment system 400 has the advantage of being a compact device that will easily fit in the footwear of the patient while providing NPWT to a wound on the bottom of a patient's foot. The first chamber 406 may be sized small enough to only cover an area slightly larger than a single wound. In some embodiments, the first chamber 406 may be sized to cover a larger area to provide treatment to several wounds at the same time. Further, the second chamber 408 may be placed under the portion of the foot to provide maximum comfort based on the individual preferences of the patient.

Figure 5:
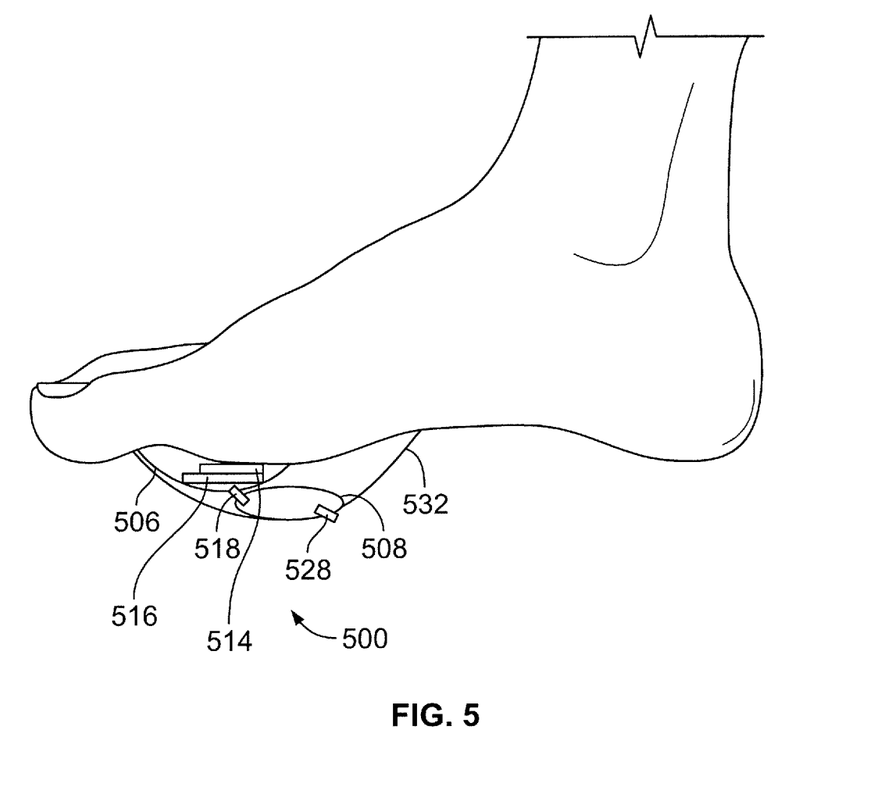
FIG. 5 is a depiction of a fifth embodiment of a NPWT system according to the invention.

Turning now to FIG. 5, a schematic embodiment of a negative pressure wound treatment system 500 is depicted as a single device configured as a single bandage. The treatment system 500 includes a first chamber 506 and a second chamber 508. The first chamber 506 includes a dressing portion 514 that is in contact with a wound and a reservoir 516. The first chamber 506 is in fluid communication with the second chamber 508 through a first valve 518. The second chamber 508 is in fluid communication with the surrounding environment through a second valve 528. An outer cover 532 contains all of the components and aids the patient or healthcare provider in applying the treatment system 500 and helps retain the treatment system 500 to the patient's foot. The treatment system 500 may include all or some of the characteristics and features of the treatment systems 100, 200, 300, 400 depicted in FIGS. 1-4. The operation of the treatment system 500 is similar to the systems 100, 200, 300, 400 as described above. The patient attaches the treatment system 500 such that the first chamber 506 is over a wound and the dressing portion 514 is in contact with the wound. The first chamber 506 may be secured with adhesive and forms a seal around the wound. The outer cover 532 may also be secured with adhesive to retain the treatment system 500 in place similar to a self-adhesive bandage. As the patient walks, the second chamber 508 is cyclically compressed. It is contemplated that the treatment system 500 may be placed to treat a wound located anywhere on the foot such that the second chamber 508 is actuated appropriately during walking. While the treatment system 500 is depicted placed under the front part of the foot, other portions (e.g., the arch, the heal, a toe) would also be acceptable as long as the first chamber 506 can create a seal around the wound and the second chamber 508 is actuated by the walking motion of the patient. It is also contemplated that the treatment system 500 may be sized to treat different sized wounds on different parts of the foot depending on the size and severity of the wound.

Figure 6:
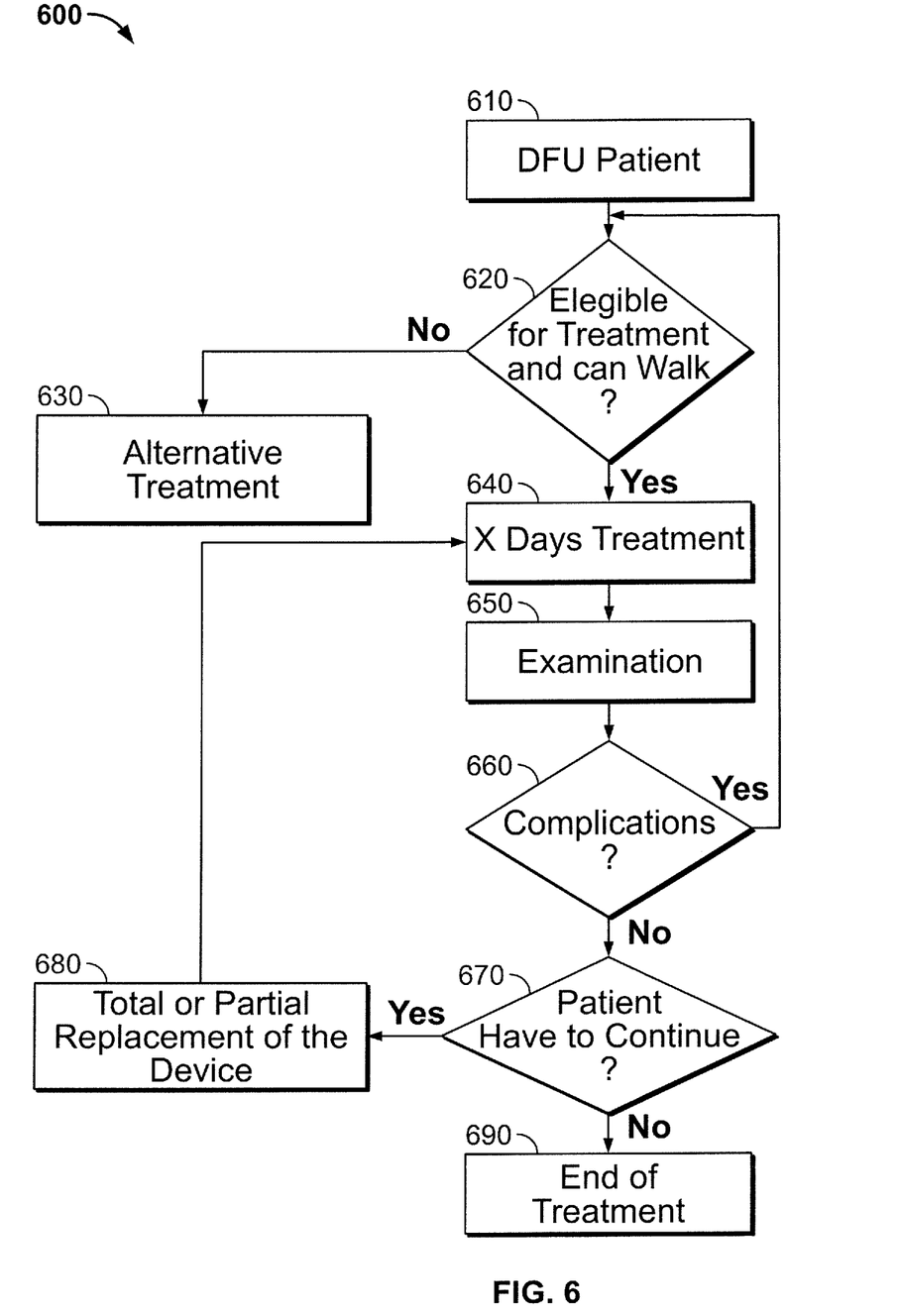
FIG. 6 is a flow chart depicting a treatment process utilizing a NPWT system according to the invention.

Turning now to FIG. 6, a flow chart depicting a NPWT process 600 for utilizing any of the treatment systems 100, 200, 300, 400, 500 to treat a patient with a DFU. The process starts out with a DFU patient 610 that needs treatment. The healthcare provider must determine if the DFU patient 610 is eligible for treatment with the one of the treatment systems 100, 200, 300, 400, 500 by deciding in block 620 if the patient can walk and if the patient meets any and all other criteria. If the patient is not eligible the healthcare provider may suggest alternative treatment in block 630. Should the healthcare provider determine the patient is eligible; the next step is to prescribe the treatment and device for X days in block 640. At this time the healthcare provider may apply the treatment system selected to the wound or give the treatment system selected to the DFU patient 610 for application later. It is contemplated that X days could be any of the values or ranges previously mentioned including from a few hours to a few weeks. Next, the DFU patient 610 is examined by the healthcare provider in block 650. The healthcare provide then must determine in block 660 if there are any unexpected complications. If there are complications, the healthcare provider may reevaluate the DFU patient in block 620 for eligibility to be treated with any of the treatment systems 100, 200, 300, 400, 500 and continue the process accordingly. If the healthcare provide does not identify any complications, a decision to continue treatment is made in block 670. If the patient does not require further treatment, the treatment is ended in block 690. However, if further treatment is required, the healthcare provider may replace the entire treatment system 100, 200, 300, 400, 500 or only a relevant portion in block 680. The process then moves back to assigning the X length of time from treatment in block 640 and repeats as described above.

Figure 7:
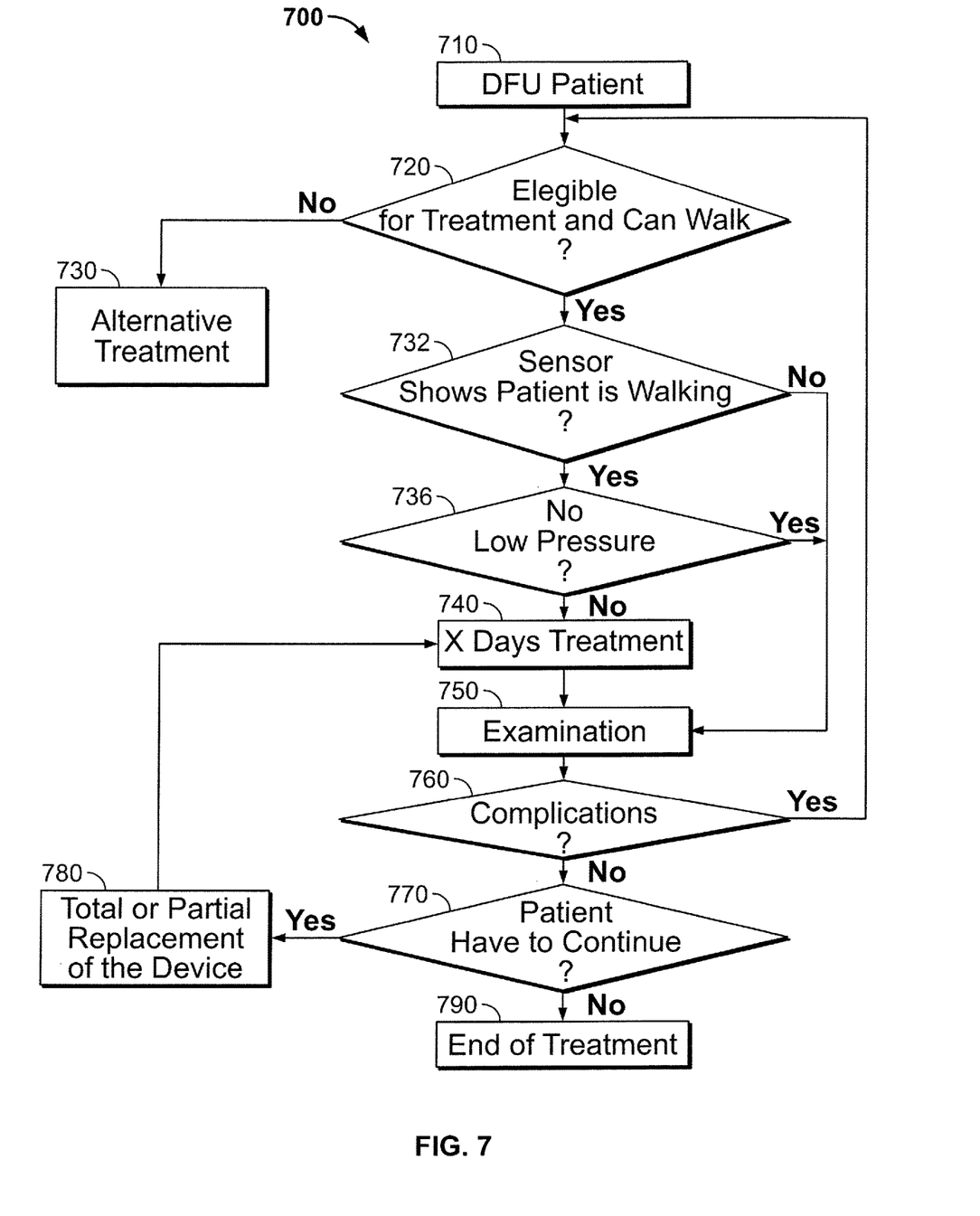
FIG. 7 is a flow chart depicting a treatment process utilizing a NPWT system including a sensor according to the invention.

FIG. 7 depicts a flowchart of a NPWT process 700 similar to the process 600 except the treatment system 100, 200, 300, 400, 500 includes at least one sensor 150 and/or an external device 155. The process 700 starts out with a DFU patient 710 that needs treatment. The healthcare provider must determine if the DFU patient 710 is eligible for treatment with the one of the treatment systems 100, 200, 300, 400, 500 by deciding in block 720 if the patient can walk and if the patient meets any and/or all other criteria. If the patient is not eligible, the healthcare provide may suggest alternative treatment in block 730. Should the healthcare provider determine the patient is eligible; the next step is to apply appropriate treatment system and determine if the sensor 150 is showing that the DFU patient 710 is walking in block 732. The process continues on to block 736 where the healthcare provider verifies that the sensor is measuring a low pressure from the walking action of the DFU patient. If during the process of blocks 732 and 736 the healthcare provide determines that the treatment system is not performing, the healthcare provider may change out the treatment system or reposition the treatment system. The process proceeds once it is determined that the treatment system is operating correctly to block 740 where the healthcare provider prescribes the treatment for X days. The next block 750 is the examination of the DFU patient 710 by the healthcare provider after the treatment time period X has elapsed. The healthcare provider then must determine in block 760 if there are any unexpected complications. If there are complications, the healthcare provider may move back in the process to block 720 to reevaluate the DFU for eligibility to be treated with any of the treatment systems 100, 200, 300, 400, 500 and continue the process accordingly. If the healthcare provide does not identify any complications, a decision to continue treatment is made in block 770. If the patient does not require further treatment, the treatment is ended in block 790. However, if further treatment is required, the healthcare provider may replace the entire treatment system or only a relevant portion in block 780. The process then moves back to assigning the X length of time from treatment in block 740 and repeats as described above.

It is contemplated that one or more aspects of the treatment system 500 provide unique advantages to a patient. Walking while wearing the treatment system 500 is easy and comfortable because of the small size. Further, the ability to only treat a single wound as opposed to the entire foot or lower leg is a significant improvement over the prior art. Treatment system 500 requires no special footwear and is easily applied by the user over a wound. The comfort and quality of life improvements provided by a patient being able to easily treat a wound located on the bottom surface of a foot is a significant advantage that should lead to better and faster healing.

In a different embodiment, any of the systems described herein may be applied wherein no wound is present to locally induce or mimic the therapeutic effects of massage.

Any of the embodiments described herein may be modified to include any of the structures or methodologies disclosed in connection with different embodiments. Further, the present disclosure is not limited to negative pressure wound treatment systems of the type specifically shown.

A negative pressure wound treatment system is presented that provides negative pressure wound therapy to a wound. Thus, a user may experience the benefit provided of improved quality of life as the wound heals while the treatment system helps prevent infection and increases blood flow to the area of the wound.

In a different embodiment, a negative pressure treatment system is presented wherein a wound or ulcer is present or not, to treat conditions as seroma plantar fasciitis, foot pain including form circulatory problems, lymphedema and neurogenic origins as foot neuropathy.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A wound healing device, the device comprising:
    a first chamber including a dressing, wherein the first chamber is configured to form a seal around a wound of a user and the dressing is in contact with the wound, and wherein the seal is around the perimeter of the first chamber; and
    a second chamber including at least one valve, wherein the second chamber is in fluid communication with the first chamber through the at least one valve, wherein actuation of the second chamber creates a negative pressure environment in the first chamber, and wherein the second chamber is configured and positioned to be actuated by the user while walking, and
    wherein the second chamber is configured to form a seal around a portion of a bottom of the user's foot and the portion includes the wound.

2. The wound healing device of claim 1, wherein the seal is formed by an adhesive around the perimeter of the first chamber.

3. The wound healing device of claim 1, wherein the first chamber collects liquid from the wound.

4. The wound healing device of claim 1, wherein the second chamber includes a reservoir configured to collect liquid from the wound.

5. The wound healing device of claim 4, wherein the reservoir comprises an absorbent material.

6. The wound healing device of claim 1, wherein the first chamber includes a reservoir configured to collect fluid from the wound.

7. The wound healing device of claim 6, wherein the reservoir comprises an absorbent material.

8. The wound healing device of claim 1, wherein the second chamber is in fluid communication with the first chamber through the at least one valve, and the second chamber is in fluid communication with a surrounding environment through a second valve.

9. The wound healing device of claim 8, wherein the at least one valve and the second valve are one-way valves.

10. The wound healing device of claim 1, wherein the first chamber and the second chamber are configured as components of a self-adhesive bandage.

11. The wound healing device of claim 1, wherein the first chamber is configured to form a seal around a wound on a portion of a user's lower extremity away from a bottom of the user's foot and the second chamber is configured to be position under a user's foot within a shoe.

12. The wound healing device of claim 11, wherein the first chamber and the second chamber are connected via a flexible tube.

13. The wound healing device of claim 12, wherein the second chamber is part of a shoe insole.

14. The wound healing device of claim 1, wherein any of the valves include a release mechanism, trigger, or switch that when activated enables or disables the generation of a negative pressure within the first chamber.

15. The wound healing device of claim 1, wherein the first chamber spans a portion of the lower surface of the foot of the user that is smaller than the entire lower surface of the foot of the user.

16. A method of treating a wound on a lower body extremity with negative pressure wound therapy, the method comprising:
    positioning a first chamber over a wound on the lower body extremity, wherein the first chamber includes a dressing configured to contact the wound;
    forming a seal around a perimeter of the first chamber;
    positioning a second chamber below the lower body extremity, where the second chamber is configured to be actuated by the lower body extremity during walking;
    positioning the second chamber within a shoe and the first and second chambers are configured as an insole device sized to fit within the shoe;
    fluidly coupling the first chamber to the second chamber through a first valve; and
    fluidly coupling the second chamber to a surrounding environment through a second valve, wherein actuation of the second chamber causes a negative pressure environment to be formed within the first chamber over the wound.

17. The method of claim 16, wherein the seal is formed around the perimeter of the first chamber with an adhesive.

18. The method of claim 16, further comprising:
    positioning the second chamber within a shoe of a user;
    positioning the first chamber away from the shoe of the user; and
    connecting the first chamber to the second chamber through a flexible tube.

19. The method of claim 16, further comprising:
collecting fluid from the wound in the first chamber, wherein the first chamber includes an absorbent reservoir.

20. The method of claim 16, further comprising:
collecting fluid from the wound in the second chamber, wherein the second chamber includes an absorbent reservoir.

21. The method of claim 16, further comprising:
positioning the first chamber adjacent the second chamber, wherein the first chamber is configured to seal around the wound located on the bottom of a foot of a user.

22. The method of claim 16, wherein:
the negative pressure environment formed within the first chamber is in the range from about 40 millimeters of mercury to about 200 mm of mercury.

23. The method of claim 16, wherein any of the valves include a release mechanism, trigger, or switch that when activated enables or disables the generation of a negative pressure within the first chamber.

\* \* \* \* \*

UNITED STATES PATENT AND TRADEMARK OFFICE
CERTIFICATE OF CORRECTION

PATENT NO. : 11,324,639 B2
APPLICATION NO. : 15/761659
DATED : May 10, 2022
INVENTOR(S) : Julian Daich et al.

It is certified that error appears in the above-identified patent and that said Letters Patent is hereby corrected as shown below:

In the Specification

Column 8, Line 24, "foamed" should be --formed--.

Signed and Sealed this
Sixth Day of September, 2022

Katherine Kelly Vidal
*Director of the United States Patent and Trademark Office*